United States Patent
Liou et al.

(10) Patent No.: US 11,103,446 B2
(45) Date of Patent: Aug. 31, 2021

(54) OPHTHALMIC DRUG DELIVERY DEVICE AND METHOD FOR FABRICATING THE SAME

(71) Applicant: Industrial Technology Research Institute, Hsinchu (TW)

(72) Inventors: Yu-Bing Liou, Hsinchu (TW); Hsin-Yi Hsu, Taoyuan (TW); Ying-Wen Shen, Miaoli County (TW); Yun-Chung Teng, Kaohsiung (TW); Yuchi Wang, New Taipei (TW); Hsin-Hsin Shen, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/731,966

(22) Filed: Dec. 31, 2019

(65) Prior Publication Data

US 2021/0196626 A1 Jul. 1, 2021

(51) Int. Cl.
*A61K 9/00* (2006.01)
*A61K 47/42* (2017.01)
*A61K 47/34* (2017.01)
*A61K 47/32* (2006.01)
*A61K 45/06* (2006.01)

(52) U.S. Cl.
CPC ............ *A61K 9/0051* (2013.01); *A61K 47/32* (2013.01); *A61K 47/34* (2013.01); *A61K 47/42* (2013.01); *A61K 45/06* (2013.01)

(58) Field of Classification Search
None
See application file for complete search history.

(56) References Cited

U.S. PATENT DOCUMENTS

| | | |
|---|---|---|
| 7,985,208 B2 | 7/2011 | Christensen |
| 8,469,934 B2 | 6/2013 | Weiner et al. |
| 8,715,712 B2 | 5/2014 | de Juan, Jr. et al. |
| 9,421,126 B2 | 8/2016 | Alster et al. |
| 9,486,362 B2 | 11/2016 | Shikamura et al. |
| 9,750,636 B2 | 9/2017 | Rubin et al. |

(Continued)

FOREIGN PATENT DOCUMENTS

| | | |
|---|---|---|
| CN | 1652686 A | 8/2005 |
| CN | 102778762 A | 11/2012 |

(Continued)

OTHER PUBLICATIONS

Taiwanese Office Action issued in Application No. 108148582 dated Dec. 9, 2020.

*Primary Examiner* — Melissa S Mercier
(74) *Attorney, Agent, or Firm* — Birch, Stewart, Kolasch & Birch, LLP

(57) ABSTRACT

An ophthalmic drug delivery device and a method for fabricating the same are provided. The ophthalmic drug delivery device includes a shield element and a drug release element. The shield element has a light transmittance more than or equal to 80%. The drug release element is an annular body so that the drug release element surrounds the shield element. The drug release element is neutral and includes a cross-linked neutral collagen, a first hydrophilic biodegradable polymer and a drug. The shield element is acidic and includes a cross-linked acidic collagen and a second hydrophilic biodegradable polymer.

20 Claims, 7 Drawing Sheets

(56) References Cited

U.S. PATENT DOCUMENTS

| | | | |
|---|---|---|---|
| 2008/0243095 A1 | 10/2008 | Kaiser et al. | |
| 2012/0022473 A1 | 1/2012 | Shikamura et al. | |
| 2014/0027571 A1 | 9/2014 | Heitel et al. | |
| 2018/0289857 A1 | 10/2018 | Rafat | |
| 2019/0374381 A1* | 12/2019 | Tai | A61K 9/0051 |
| 2020/0409177 A1* | 12/2020 | Tai | G02C 7/041 |

FOREIGN PATENT DOCUMENTS

| | | |
|---|---|---|
| CN | 103619327 A | 3/2014 |
| CN | 103917202 A | 7/2014 |
| TW | M408354 U1 | 8/2011 |
| TW | I538935 B | 6/2016 |
| TW | I635877 B | 9/2018 |
| WO | WO 2010/052694 A2 | 7/2014 |

* cited by examiner

OPHTHALMIC DRUG DELIVERY DEVICE AND METHOD FOR FABRICATING THE SAME

TECHNICAL FIELD

The disclosure relates to an ophthalmic drug delivery device and a method for fabricating the same.

BACKGROUND

The pharmaceutical industry has developed a variety of techniques for delivering ophthalmic compositions to the eye (particularly those that include therapeutic agents). Typical ophthalmic drug delivery techniques include topical application of ophthalmic compositions to the eye (e.g., by drops administered directly onto the eye) and intravitreal injections (e.g., delivery of ophthalmic compositions to the vitreous of the eye with a needle, such as a syringe). There are problems in the case of two ophthalmic drug delivery techniques. (1) It is inconvenient in that the ophthalmic compositions (such as drugs for glaucoma treatments) should be frequently administrated to maintain a constant concentration which may maintain the treatment's effectiveness. (2) There are also some problems in that the medicine may be washed away from an eyeball by eye-blinking motions, and thus the maintenance time for the effective treatment concentration is shortened. In addition, (3) a low medicine concentration remains for a long time, and thus the effectiveness of the treatment is reduced.

Therefore, instead of eye drops or eye bath drops, ophthalmic ointment are widely used as viscous semi-solid medicines. Compared with the eye drops, since the medicine in the form of ointment type has a relatively long contact time with the eyeball, the opportunity of the medicine to be absorbed is increased. However, after applying the ointment, the patient's vision is considerably reduced, and the entire portion of the eyeball and the periphery of the eye may feel uncomfortable due to the presence of foreign objects.

Moreover, the industry has also proposed the alternative treatment schemes, in which components containing or impregnated with drugs have been placed under the eyelid. However, due to the disadvantages of poor comfort and easy interference with vision, the patient's acceptance of this ophthalmic device for drug delivery is limited.

Accordingly, a novel ophthalmic drug delivery device for applying the ophthalmic composition to intraocular tissues over a long time period is desired.

SUMMARY

According to embodiments of the disclosure, the disclosure provides an ophthalmic drug delivery device. The ophthalmic drug delivery device includes a shield element, which is adapted to be positioned onto a visual region of a cornea, in which the shield element has a light transmittance more than or equal to 80%, and a drug release element, which is adapted to be positioned onto a region surrounding the cornea, and the region is outside the cornea, in which the drug release element is an annular body, and the drug release element surrounds the shield element. In addition, the drug release element is neutral and can include a cross-linked neutral collagen, a first hydrophilic biodegradable polymer, and a drug. The shield element is acidic and can include a cross-linked acidic collagen and a second hydrophilic biodegradable polymer.

The disclosure also provides a method for fabricating an ophthalmic drug delivery device. The method for fabricating an ophthalmic drug delivery device may include the following steps: providing a first aqueous solution, in which the first aqueous solution may include water, a first collagen, a first hydrophilic biodegradable polymer, a first acidic substance, and a drug, and in which the first aqueous solution has a pH value of 2 to 5; pouring the first aqueous solution into a first mold, and then the first mold is cooled down to a temperature of 1° C. to 10° C.; pouring a second aqueous solution into the first mold, in which the first aqueous solution is automatically stratified with the second aqueous solution in the first mold, in which the first aqueous solution is served as a lower-layer liquid, and the second aqueous solution is served as an upper-layer liquid, and in which the second aqueous solution can include an alkali metal hydroxide and water, and the second aqueous solution can have a pH value of 9 to 11; standing the first mold to transfer the first aqueous solution into a first layer, in which the first layer can have a central region and an annular region, and the annular region surrounds the central region and is coaxial with the central region; removing the central region from the first layer so that the remaining first layer has a through hole after removing the second aqueous solution from the first mold; filling the through hole with the third aqueous solution, in which the third aqueous solution can include water, a second collagen, a second acidic substance, and a second hydrophilic biodegradable polymer, in which the third aqueous solution can have a pH value of 2 to 5; subjecting the third aqueous solution to a drying process, to obtain a second layer, in which the first layer and the second layer constitute a composite film, and in which the second layer can be acidic; disposing the composite film in a second mold to obtain a molded film after molding; and, subjecting the composite film to a cross-linking process by a cross-linking agent to obtain the ophthalmic drug delivery device.

A detailed description is given in the following embodiments with reference to the accompanying drawings.

DETAILED DESCRIPTION

Figure 1:
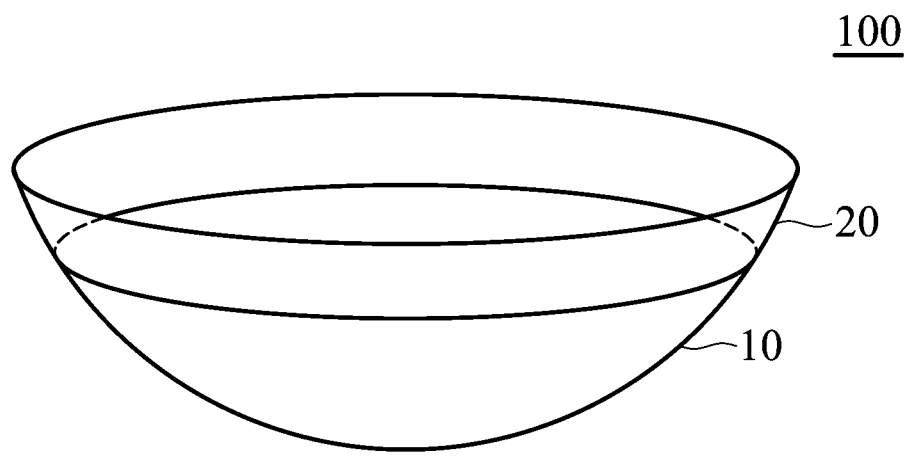
FIG. 1 is a schematic diagram illustrating an ophthalmic drug delivery device according to an embodiment of the disclosure.

The ophthalmic drug delivery device and the method for fabricating the same of the disclosure are described in detail in the following description. In the following detailed description, for purposes of explanation, numerous specific details and embodiments are set forth in order to provide a thorough understanding of the disclosure. The specific elements and configurations described in the following detailed description are set forth in order to clearly describe the disclosure. It will be apparent, however, that the exemplary embodiments set forth herein are used merely for the purpose of illustration, and the inventive concept may be embodied in various forms without being limited to those exemplary embodiments.

It should be noted that the elements or devices in the drawings of the disclosure may be present in any form or configuration known to those skilled in the art. The use of ordinal terms such as "first", "second", "third", etc., in the disclosure to modify an element does not by itself connote any priority, precedence, or order of one claim element over another or the temporal order in which it is formed, but are used merely as labels to distinguish one claim element having a certain name from another element having the same name (but for use of the ordinal term) to distinguish the claim elements.

The disclosure provides a drug delivery device, in which the drug delivery device includes a shield element and a drug release element. Since the shield element of the drug delivery device is made of biodegradable materials and exhibits high light transmittance (greater than 80%), the shield element can be positioned onto a visual region of a cornea without interfering the vision of the user and can protect, and can protect the wound from contact during healing while the drug delivery device is disposed under the eyelids and external to the eyeball. Due to the drug release element, the drug delivery device can be released in a sustained manner during a relatively long time period, and thus the effective time of a single dose treatment is extended and the number of drug administration is reduced, and the goal of eye disease treatment may be achieved. In addition, the ophthalmic drug release element can be positioned onto a region surrounding the cornea, and the region is outside the visual region, while the drug delivery device is disposed under the eyelids and external to the eyeball. As a result, even if the drug release element exhibits relatively low light transmittance, the vision of the user would not be impaired.

According to embodiments of the disclosure, the disclosure provides an ophthalmic drug delivery device. FIG. 1 is a schematic diagram illustrating an ophthalmic drug delivery device 100 according to an embodiment of the disclosure. As shown in FIG. 1, the ophthalmic drug delivery device 100 includes a shield element 10 and a drug release element 20. The ophthalmic drug delivery device 100 has a curvature radius ranging from 6 mm to 10 mm. The ophthalmic drug delivery device 100 can be disposed under the eyelids and external to the eyeball of a patient, and in close contact with the surface of eyeball without displacement. While the drug delivery device 100 is disposed under the eyelids and external to the eyeball, the shield element 10 is adapted to be positioned onto a visual region of a cornea, and the drug release element 20 is adapted to be positioned onto a region surrounding the cornea and the region is outside the visual region.

Figure 2:
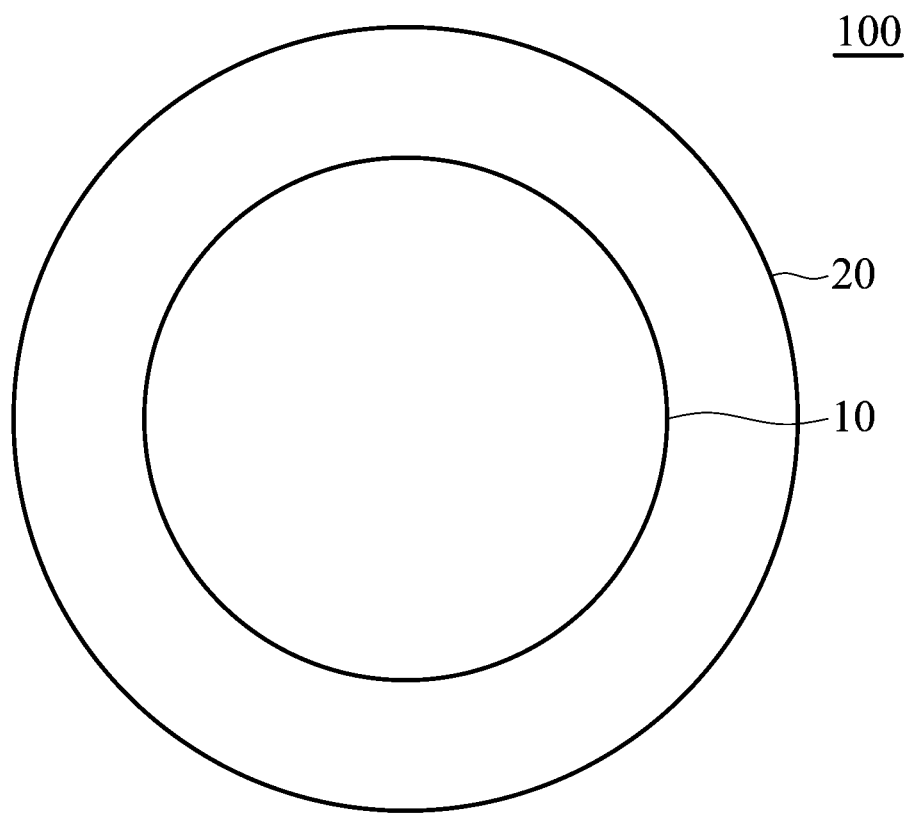
FIG. 2 is a top-view diagram of the ophthalmic drug delivery device 100 as disclosed in FIG. 1.
Figure 3:
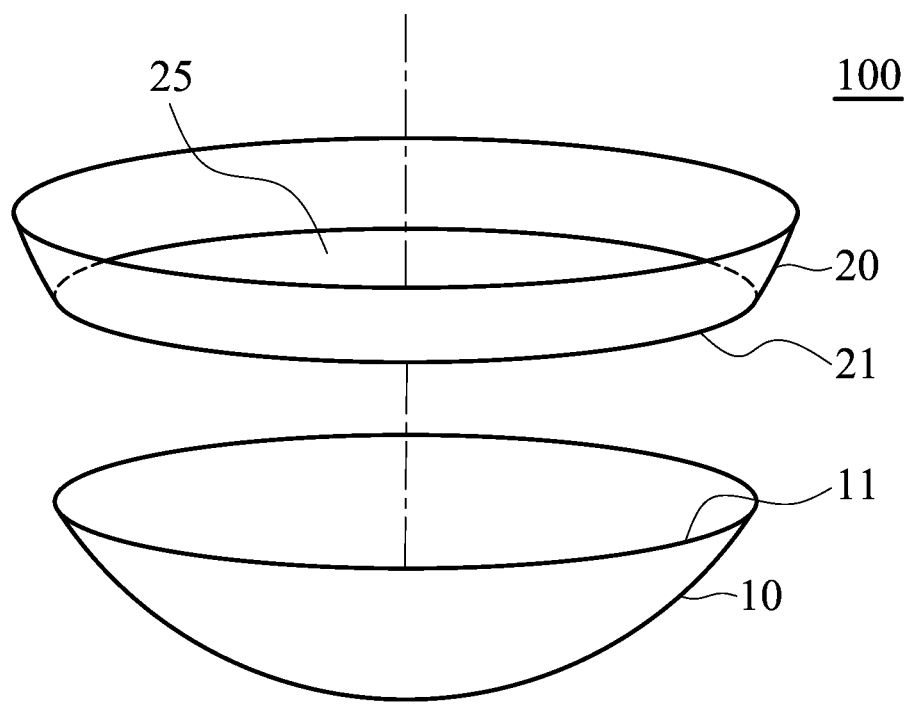
FIG. 3 is an explosion diagram of the ophthalmic drug delivery device 100 as disclosed in FIG. 1.

FIG. 2 is a top-view schematic diagram of the ophthalmic drug delivery device 100 as disclosed in FIG. 1. As shown in FIG. 2, an orthogonal projection of the shield element 10 onto a horizontal surface is circular, and the drug release element 20 is an annular body, in which the drug release element 20 surrounds the shield element 10, and the drug release element 20 is coaxial with the shield element 10. FIG. 3 is an explosion diagram of the ophthalmic drug delivery device 100 as disclosed in FIG. 1. As shown in FIG. 3, the drug release element 20 can be an annular body with a through hole 25, and the drug release element 20 has an inside edge 21. The shield element 10 has an outside edge 11, in which the inside edge 21 directly contacts to and corresponds with the outside edge 11 (i.e. an orthogonal projection of the inside edge 21 onto a horizontal surface completely overlaps an orthogonal projection of the outside edge 11 onto the horizontal surface).

According to embodiments of the disclosure, the drug release element 20 includes a cross-linked neutral collagen, a first hydrophilic biodegradable polymer, and a drug. According to embodiments of the disclosure, as regards the structure, the drug release element 20 can be a multi-layered structure constituted by the cross-linked neutral collagen and the first hydrophilic biodegradable polymer, in which the drug is uniformly dispersed and embedded in the multi-layered structure. As regards the material, the drug release element 20 can be a composite material at least constituted by a cross-linked neutral collagen and a first hydrophilic biodegradable polymer, and a drug is uniformly dispersed in the composite material. Since the drug is embedded in a layered structure constituted by the cross-linked neutral collagen and the first hydrophilic biodegradable polymer, the drug release element 20 can release the drug with a constant concentration to the intraocular tissues for a predetermined time period when the ophthalmic drug delivery device is disposed on the eyeball of the patient, thereby achieving long-term drug delivery with constant rate release.

In addition, the cross-linked neutral collagen can be fibrous, and have a fiber length of between about 1.5 mm and 50 mm, such as between about 5 mm to 45 mm, between about 10 mm to 40 mm, between about 15 mm to 30 mm, but the disclosure is not limited thereto. According to embodiments of the disclosure, in the multi-layered structure, there are at least ten layers (stacked each other) per 5 μm of thickness. Each stacked layer has a thickness of between 0.1 μm to 1 μm.

Furthermore, According to embodiments of the disclosure, the weight ratio of the cross-linked neutral collagen to the first hydrophilic biodegradable polymer can be ranging from about 1:3 to 9:1, such as from about 1:3 to 1:1, from about 1:1 to 3:1, or from about 3:1 to 9:1, but the disclosure is not limited thereto. When the weight ratio of the cross-linked neutral collagen to the first hydrophilic biodegradable polymer is too low, the film is relatively brittle and apt to dissolve in water (rather than forming a film) after water absorption due to the absence of fibrous structure. Conversely, when the weight ratio of the cross-linked neutral collagen to the first hydrophilic biodegradable polymer is too high, the water absorption rate of the film is decreased.

Furthermore, according to embodiments of the disclosure, the amount of the drug can be, but is not limited to, ranging from 0.01 wt % to 20 wt %, such as 0.02 wt %, 0.05 wt %, 0.1 wt %, 0.2 wt %, 0.5 wt %, 1 wt %, 3 wt %, 5 wt %, 10 wt %, or 15 wt %, based on the total weight of the neutral collagen and the first hydrophilic biodegradable polymer. In addition, according to embodiments of the disclosure, the cross-linked neutral collagen can have a pH value of 6.5 to 7.5, such as 6.7 to 7.4, 6.8 to 7.2, but the disclosure is not limited thereto.

According to embodiments of the disclosure, drug release element 20 can consist of cross-linked neutral collagen, a first hydrophilic biodegradable polymer, and a drug.

According to embodiments of the disclosure, the first hydrophilic biodegradable polymer can be selected from a group consisting of polyvinyl alcohol (PVA), polyethylene glycol/polyethylene oxide (PEG/PEO) and polyvinylpyrrolidone (PVP). According to embodiments of the disclosure, the first hydrophilicity polymer can have a molecular weight of about 300 to 1,500,000. The degradation rate of the composite material (constituted by the first hydrophilic biodegradable polymer and collagen) can be controlled by modifying the molecular weight of the hydrophilic biodegradable polymer. For example, the hydrophilic biodegradable polymers with a relatively low molecular weight (such as the molecular weight of between about 300 and 60,000) results in a high degradation rate of the composite material. In contrast, the hydrophilic biodegradable polymers with a relatively high molecular weight (such as the molecular weight of between 100,000 and 1,500,000) results in a slow degradation rate of the composite material. Specifically, when the first hydrophilic biodegradable polymer is polyvinyl alcohol (PVA), the first hydrophilic biodegradable polymer can have a molecular weight of between about 10,000 and 200,000; when the first hydrophilic biodegradable polymer is polyethylene glycol/polyethylene oxide (PEG/PEO), the first hydrophilic biodegradable polymer can have a molecular weight of between about 300 and 150,000; and, when the first hydrophilic biodegradable polymer is polyvinylpyrrolidone (PVP), the first hydrophilic biodegradable polymer can have a molecular weight of between about 10,000 and 1,500,000. In the disclosure, the above-mentioned molecular weight of polymer means weight average molecular weight.

According to embodiments of the disclosure, the drug includes, but is not limited to, any drug or active factor suitable for treating eye disease or repairing intraocular cells. According to embodiments of the disclosure, the drug can be a drug for glaucoma therapy and includes alpha agonist (such as apraclonidine), beta blockers (such as timolol maleate, betaxolol, levobunolol, atenolol, metipranolol, or timolol hemihydrate), cholinergics (such as pilocarpine, or carbachol), prostaglandin analogs (such as travoprost, bimatoprost, tafluprost, or latanoprost), or Rho kinase inhibitor (such as netarsudil). Further, according to embodiments of the disclosure, the drug can be a drug useful for treating xerophthalmia and includes polyvinyl alcohol hypromellose, glycerine, pegaptanib, propylene glycol, tetryzoline, cyclosporine, doxycicine, vitamin D3, quinethazone, hydroxypropyl cellulose, polyvinylpyrrolidone, chlorobutanol, bepotastine besilate, lifitegrast, omega-3 fatty acids, flaxseed oil, carboxymethyl cellulose, hyaluronic acid, hydroxypropyl-guar, macrolide, tetracycline, tacrolimus, acetylcysteine, vitamin A, carbomer, triglycerides, fluorometholone, loteprednol, fluocinolone, dexamethasone, difluprednate, triamcinolone, prednisolone, or rimexolone. Furthermore, according to embodiments of the disclosure, the drug can be an antibiotic drug or anti-inflammatory drug and includes gentamicin, tobramycin, besifloxacin, ciprofloxacin, gatifloxacin, levofloxacin, moxifloxacin, ofloxacin, azithromycin, erythromycin, bacitracin, natamycin, neomycin, polymyxin B, trimethoprim, sulfacetamide, bromfenac, ketorolac, nepafenac, flurbiprofen, or diclofenac.

According to embodiments of the disclosure, the drug release element 20 can further include a metal oxide, in which the metal oxide doped in the drug release element 20. The metal oxide can be zinc oxide or iron oxide or a combination thereof. According to embodiments of the disclosure, the amount of the metal oxide can be 0.1%-50%, such as 0.2%-50%, 0.5%-50%, 1%-50%, 1%-40%, or 1%-30%, based on the weight of the drug release element. Doped with the metal oxide in the drug release element 20 can enhance the sustained release ability for a drug of the drug release element 20. When the amount of the doped metal oxide is too low, the sustained release ability of the drug release element 20 is not improved obviously. When the amount of the doped metal oxide is too high, a material including a metal oxide with a relatively high concentration may exhibit toxicity and does not be suitable for use in ophthalmic drug delivery device.

According to embodiments of the disclosure, the drug release element is a product obtained by subjecting a first layer to a cross-linking process in the presence of a cross-linking agent, in which the first layer can be a cured product of a neutral aqueous solution, and the neutral aqueous solution can include water, a first collagen, a first hydrophilic biodegradable polymer, and a drug. According to embodiments of the disclosure, the neutral aqueous solution can have a pH value of 6.5 to 7.5. Since the collagen for forming the drug release element 20 is subjected to a cross-linking process in a neutral condition (i.e. the collagen has a pH value of 6.5 to 7.5), the drug release element 20 of the disclosure can achieve the effect of long-term drug delivery with constant rate release.

According to embodiments of the disclosure, the shield element 10 includes a cross-linked acidic collagen and a second hydrophilic biodegradable polymer in order to force the shield element 10 having a light transmittance greater than or equal to 80% (such as greater than or equal to 85%, or greater than or equal to 90%). According to embodiments of the disclosure, the shield element 10 can have a multi-layered structure constituted by the cross-linked acidic collagen and the second hydrophilic biodegradable polymer. The cross-linked acidic collagen can be fibrous, and have a fiber length of between about 1.5 mm and 50 mm, such as between about 5 mm to 45 mm, between about 10 mm to 40 mm, between about 15 mm to 30 mm, but the disclosure is not limited thereto. According to embodiments of the disclosure, in the multi-layered structure, there are at least ten layers (stacked each other) per 5 μm of thickness. Each stacked layer has a thickness of between 0.1 μm to 1 μm.

Furthermore, according to embodiments of the disclosure, the weight ratio of the cross-linked acidic collagen to the second hydrophilic biodegradable polymer can be ranging from about 1:3 to 9:1, such as from about 1:3 to 1:1, from about 1:1 to 3:1, or from about 3:1 to 9:1, but the disclosure is not limited thereto. When the weight ratio of the cross-linked acidic collagen to the second hydrophilic biodegradable polymer is too low, the film is relatively brittle and apt to dissolve in water (rather than forming a film) after water absorption due to the absence of fibrous structure. Conversely, when the weight ratio of cross-linked acidic collagen to the second hydrophilic biodegradable polymer is too high, the water absorption rate of the film is decreased. According to embodiments of the disclosure, the cross-linked acidic collagen can have a pH value of 2 to 5, such as about 2.5, 3, 4, or 4.5, but the disclosure is not limited thereto.

According to embodiments of the disclosure, the shield element 10 can consist of the cross-linked acidic collagen and the second hydrophilic biodegradable polymer.

According to embodiments of the disclosure, the second hydrophilic biodegradable polymer can be selected from a group consisting of polyvinyl alcohol (PVA), polyethylene glycol/polyethylene oxide (PEG/PEO) and polyvinylpyrrolidone (PVP). According to embodiments of the disclosure, the second hydrophilic polymer can have a molecular weight ranging from about 300 to 1,500,000. The degradation rate of the composite material can be controlled by adjusting the molecular weight of the hydrophilic biodegradable polymer. For example, the hydrophilic biodegradable polymers with a relatively low molecular weight (such as the molecular weight of between about 300 and 60,000) results in a high degradation rate of the composite material.

In addition, the hydrophilic biodegradable polymers with a relatively high molecular weight (such as the molecular weight of between about 100,000 and 1,500,000) results in a slow degradation rate of the composite material. Specifically, when the second hydrophilic biodegradable polymer is polyvinyl alcohol (PVA), the second hydrophilic biodegradable polymer can have a molecular weight of between about 10,000 and 200,000; when the second hydrophilic biodegradable polymer is polyethylene glycol/polyethylene oxide (PEG/PEO), the second hydrophilic biodegradable polymer can have a molecular weight of between about 300 and 150,000; and, when the second hydrophilic biodegradable polymer is polyvinylpyrrolidone (PVP), the second hydrophilic biodegradable polymer can have a molecular weight of between about 10,000 and 1,500,000. In the disclosure, the above-mentioned molecular weight of polymer means weight average molecular weight.

According to embodiments of the disclosure, the shield element 10 can be a product obtained by subjecting a second layer to a cross-linking process in the presence of a cross-linking agent, in which the second layer is formed by drying an acidic aqueous solution, and the acidic aqueous solution can include water, a second collagen, and a second hydrophilic biodegradable polymer. According to embodiments of the disclosure, the acidic aqueous solution can have a pH value of 2 to 5. Since the collagen for forming the shield element 10 is subjected to a cross-linking process in an acidic condition (i.e. the collagen has a pH value of 2 to 5), the shield element 10 of the disclosure exhibits high light transmittance (greater than or equal to 80%, such as greater than or equal to 85%, or greater than or equal to 90%). According to embodiments of the disclosure, the above-mentioned first hydrophilic biodegradable polymer and the above-mentioned second hydrophilic biodegradable polymer can be the same or different.

According to embodiments of the disclosure, the goal for performing a cross-linking process is to decrease the degradation rate of the composite material constituted by the collagen and hydrophilic biodegradable polymer. The above-mentioned cross-linking process can be a chemical cross-linking process with a cross-linking agent. The cross-linking agent can be, but is not limited to, aldehyde-based cross-linking agent, such as formaldehyde, glutaraldehyde, glyoxal, malondialdehyde, succinyl dialdehyde, phthalaldehyde, dialdehyde starch, polyacrolein, polymethacrolein, or a combination thereof. Due to the use of aldehyde as a cross-linking agent, the collagen of the composite material can be further cross-linked via the chemical cross-linking process.

Figure 4:
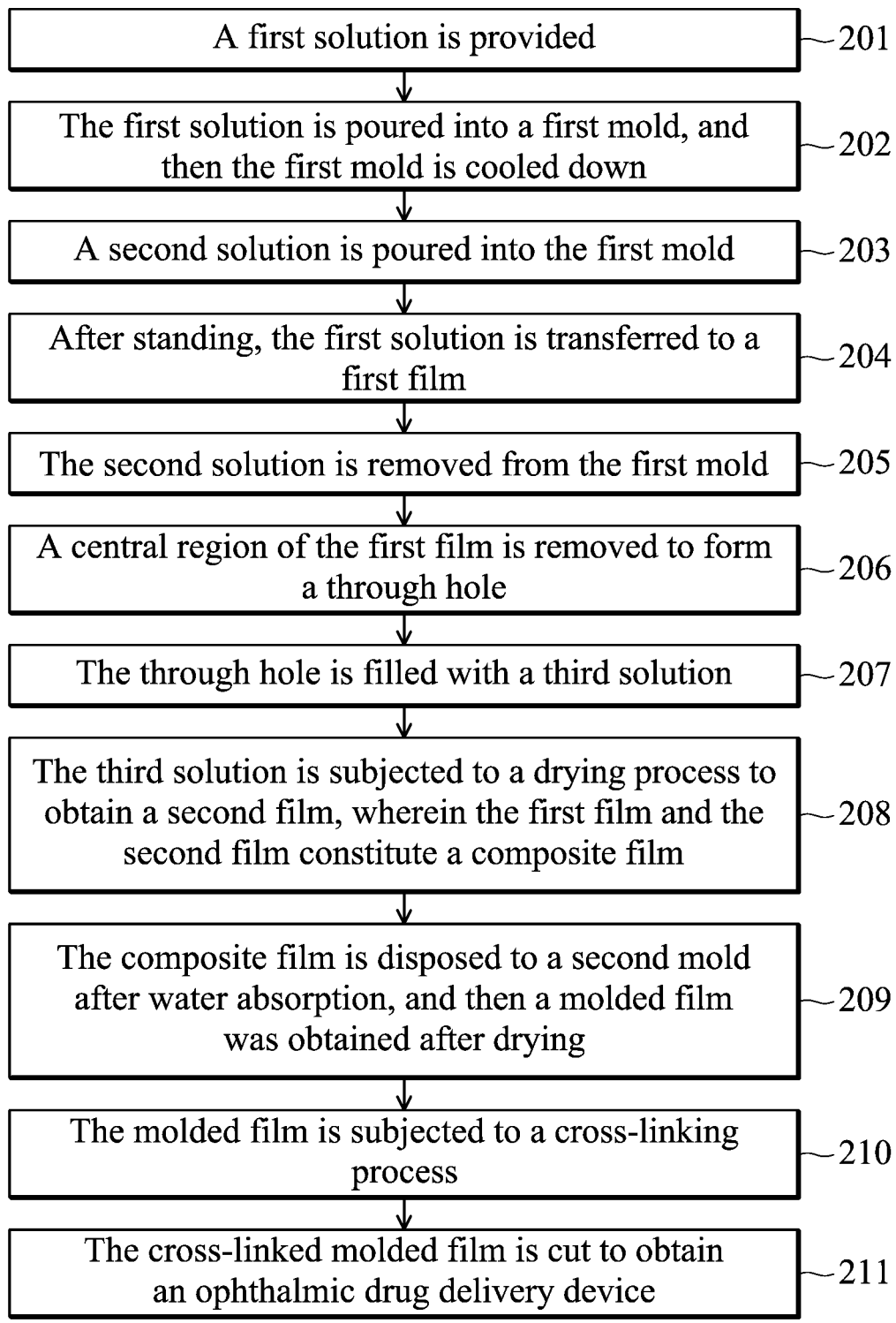
FIG. 4 is a flow chart illustrating a method 200 for fabricating an ophthalmic drug delivery device according to an embodiment of the disclosure.

According to embodiments of the disclosure, the disclosure also provides a method for fabricating the ophthalmic drug delivery device of the disclosure. Please refer to FIG. 4 and FIGS. 5A-5H simultaneously, FIG. 4 is a flow chart illustrating a method 200 for fabricating an ophthalmic drug delivery device according to an embodiment of the disclosure, and FIG. 5A-5H are schematic cross-sectional views illustrating the method 200 for fabricating the ophthalmic drug delivery device of the disclosure.

Figure 5A:
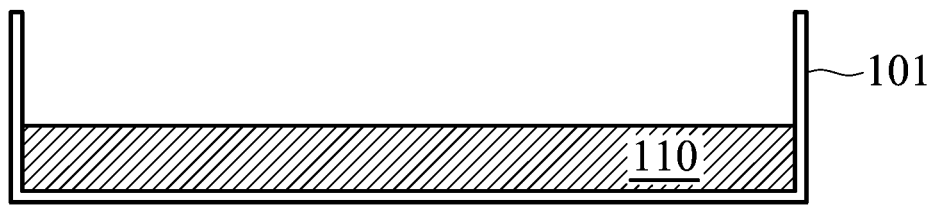
FIG. 5A-5H are schematic cross-sectional views illustrating the method 200 for fabricating an ophthalmic drug delivery device of the disclosure.

The method for fabricating an ophthalmic drug delivery device 200 of the disclosure includes following steps. First, a first aqueous solution (step 201) is provided, in which the first aqueous solution can include water, a first collagen, a first hydrophilic biodegradable polymer, a first acidic substance, and a drug, and the first aqueous solution can have a pH value of 2 to 5. Next, the first aqueous solution 110 is poured into a first mold 101, and the first mold 101 is cooled down to a temperature of 1° C. to 10° C. (step 202), as shown in FIG. 5A. In this step, due to the intermolecular charge repulsion and the hydrogen bond interaction between collagen and water, the collagen fiber is apt to be dissolved in an acidic solution so that the collagen fiber can be in a fully extended state and can be uniformly dispersed in the solution. As a result, due to the fiber length being longer than 1.5 mm (i.e. strip-shaped fiber, rather than flocculent fiber), the collagen fiber can be precipitated and stacked regularly during drying, resulting in the obtained composite material (constituted by the first collagen and the first hydrophilic biodegradable polymer) having a multi-layered structure.

Figure 5B:
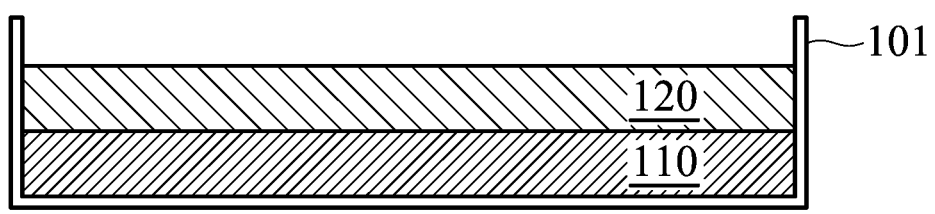
Figure 5C:
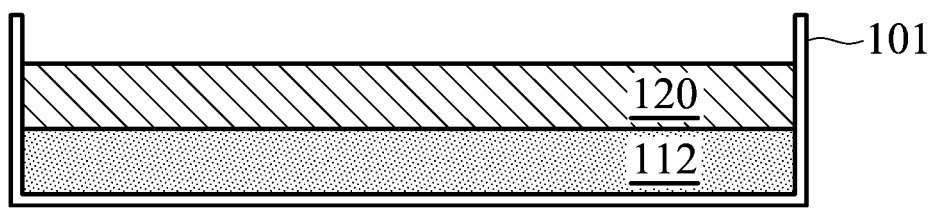

Next, a second aqueous solution 120 is poured into a first mold 101 (step 203), in which the first aqueous solution 110 is automatically stratified with the second aqueous solution 120 in the first mold 101, as shown in FIG. 5B. The first aqueous solution 110 is served as a lower-layer liquid, and the second aqueous solution 120 is served as an upper-layer liquid, in which the second aqueous solution can include an alkali metal hydroxide and water, and the second aqueous solution can have a pH value of 9 to 11. Next, as shown in FIG. 5C, the first mold 101 is stood to transfer the first aqueous solution 110 into a first layer 112 (step 204), in which the first layer 112 has a central region 113 and an annular region 115, and the annular region 115 surrounds the central region 113 and is coaxial with the central region 113. According to embodiments of the disclosure, the first mold 101 is stood at a temperature of 1° C. to 10° C. for 12 hours to 36 hours. During standing, since the hydroxyl anion of the second aqueous solution 120 neutralizes the hydron of the first aqueous solution, the pH of the first aqueous solution gradually increases from acidic to neutral. Meanwhile, the composite material (constituted by the first collagen and the first hydrophilic biodegradable polymer) is generally precipitated and insoluble in water. Therefore, the first aqueous solution 110 is transferred to the first layer 112.

Figure 5D:
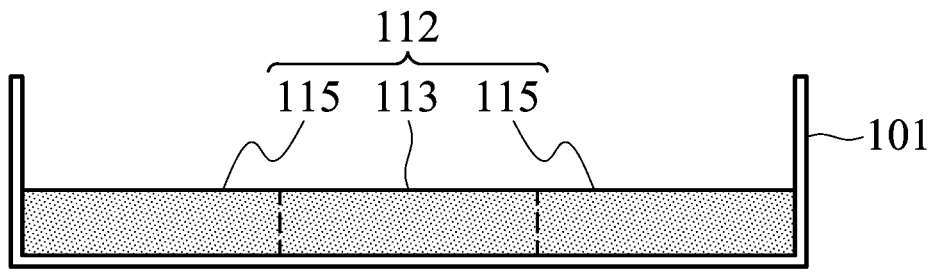
Figure 5E:
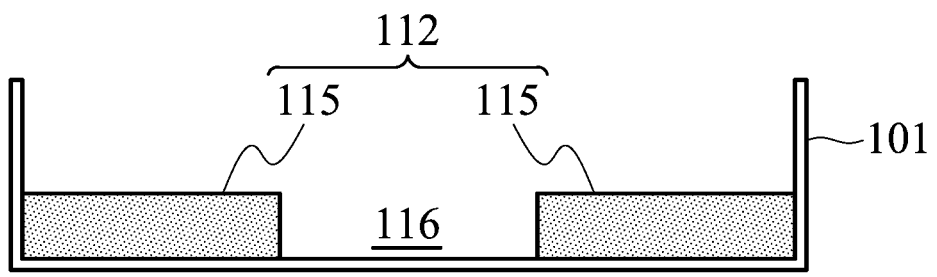

Next, as shown in FIG. 5D, the second aqueous solution 120 is removed from the first mold 101 (step 205). As shown in FIG. 5E, the central region 113 of the first layer 112 is removed so that the remaining first layer has a through hole 116 (step 206). According to embodiments of the disclosure, the through hole 116 is a circular hole with a diameter of about 6 mm to 10 mm, such as of about 6.5 mm to 9.5 mm, of about 7 mm to 9 mm, of about 7.5 mm to 8.5 mm, of about 7 mm, of about 8 mm, of about 9 mm, but the disclosure is not limited thereto.

Figure 5F:
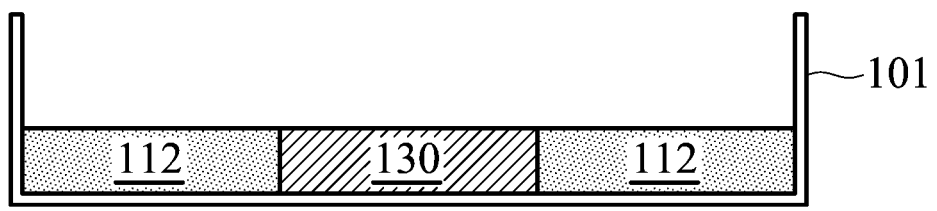

Next, as shown in FIG. 5F, a third solution 130 is filled into the through hole 116 (step 207), in which the third aqueous solution 130 includes water, a second collagen, a second acidic substance, and a second hydrophilic biodegradable polymer. The third aqueous solution can have a pH value of about 2 to 5. In this step, due to the intermolecular charge repulsion and the hydrogen bond interaction between collagen and water, the collagen fiber can be in a fully extended state and can be uniformly dispersed in the acidic solution. As a result, due to the fiber length being longer than 1.5 mm (i.e. strip-shaped fiber, rather than flocculent fiber), the collagen fiber can be precipitated and stacked regularly during drying, resulting in the obtained composite material (constituted by the second collagen and the second hydrophilic biodegradable polymer) having a multi-layered structure.

Figure 5G:
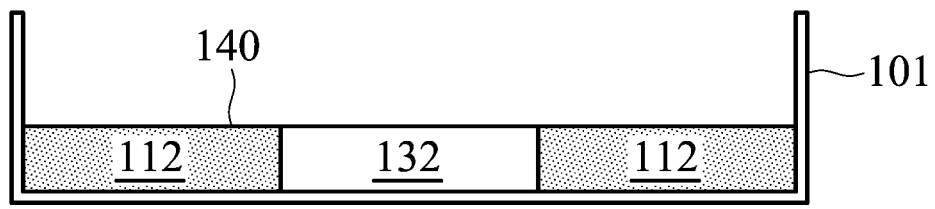

Next, as shown in FIG. 5G, the third solution 130 is subjected to a drying process to obtain a second layer 132, in which the first layer 112 and the second layer 132 constitute a composite film 140 (step 208). Herein, the first layer 112 is neutral (having a pH value of 6.5 to 7.5) and the second layer 132 is acidic (having a pH value of 2 to 5).

Figure 5H:
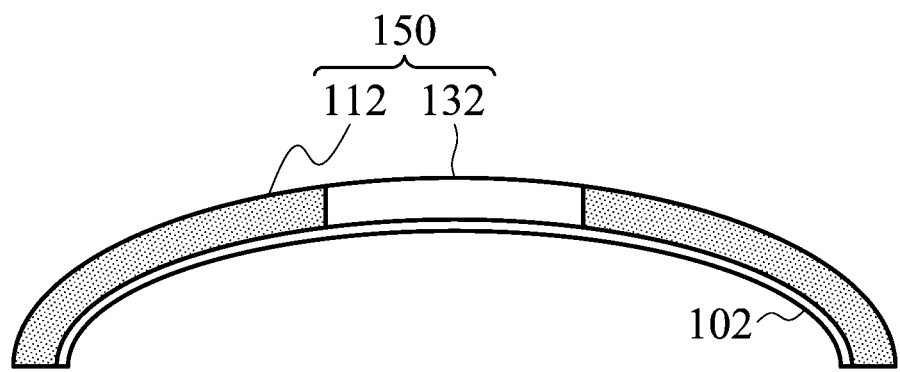

Next, as shown in FIG. 5H, the composite film 140 (after water absorption) is disposed in a second mold 102, and then is subjected to a drying process to obtain a molded film 150 after molding (step 209). Next, the molded film 150 undergoes a cross-linking reaction in the presence of a cross-linking agent (step 210). After the cross-linking reaction, the result can be optionally cut to obtain an ophthalmic drug delivery device (step 211), in which the ophthalmic drug delivery device has a diameter of 12 mm to 16 mm, a curvature radius of 6 mm to 10 mm, and a thickness of 50 μm to 500 μm.

According to embodiments of the disclosure, the preparation of the first aqueous solution 110 can include following steps. First, the first collagen, the first hydrophilic biodegradable polymer and the drug are dissolved in water to obtain a first mixture, in which the weight ratio of the first collagen to the first hydrophilic biodegradable polymer can be 1:3 to 9:1, and the amount of the drug is ranging from 0.01 wt % to 20 wt %, based on the total weight of the first collagen and the first hydrophilic biodegradable polymer. Next, the first acidic substance (or an aqueous solution including the first acidic substance) is added into the first mixture until the obtained first aqueous solution has a pH value of 2 to 5. According to embodiments of the disclosure, the first aqueous solution can have a solid content of 0.5 wt % to 10 wt % (such as about 1 wt %, 2 wt %, 4 wt %, 5 wt %, 7 wt %, or 9 wt %). Herein, the solid content means the weight percentage of all components except water. In addition, according to embodiments of the disclosure, the first acidic substance can be selected from a group consisting of hydrochloric acid, phosphoric acid and lactic acid.

According to embodiments of the disclosure, the second aqueous solution 120 further includes a metal oxide aqueous solution. According to embodiments of the disclosure, the preparation of the second aqueous solution 120 can include following steps. An alkali metal hydroxide aqueous solution is provided, in which the concentration of the alkali metal hydroxide aqueous solution can be about 0.1 M to 2 M (such as about 0.3 M, 0.5 M, 0.8 M, 1 M, 1.3 M, 1.5 M, or 1.8 M). Next, the metal oxide is dissolved in the alkali metal hydroxide aqueous solution to obtain the second aqueous solution, in which the amount of the metal oxide can be about ranging from 0.5 wt % to 2 wt % (such as about 0.8 wt %, 1 wt %, or 1.5 wt %), based on the second aqueous solution. The obtained second aqueous solution has a pH value of 9 to 11. According to embodiments of the disclosure, the alkali metal hydroxide can be selected from a group consisting of lithium hydroxide, sodium hydroxide, and potassium hydroxide.

According to embodiments of the disclosure, the amount of the second aqueous solution 120 is determined based on the amount of the first aqueous solution which has to be neutralized to neutral. According to embodiments of the disclosure, after removing the second aqueous solution from the first mold, the first layer may be further washed with water until the first layer is neutral.

According to embodiments of the disclosure, the preparation of the third aqueous solution can include following steps. The second collagen and the second hydrophilic biodegradable polymer are dissolved in water to obtain a third mixture, in which the weight ratio of the second collagen to the second hydrophilic biodegradable polymer can be about ranging from 1:3 to 9:1. Next, the second acidic substance is added into the third mixture until the third aqueous solution has a pH value of 2 to 5. According to embodiments of the disclosure, the third aqueous solution can have a solid content about ranging from 0.5 wt % to 10 wt %. According to embodiments of the disclosure, the second acidic substance can be selected from a group consisting of hydrochloric acid, phosphoric acid and lactic acid.

According to embodiments of the disclosure, since the first collagen of the first layer 112 undergoes a cross-linking reaction in a neutral condition (i.e. the first collagen is neutral when subjected to a cross-linking process), the obtained drug release element exhibits enhanced sustained release ability, thereby achieving the effect of long-term drug delivery with constant rate release. Herein, the cross-linked neutral collagen of the disclosure means that the collagen undergoes a cross-linking reaction in a neutral condition (i.e. the collagen is neutral when subjected to a cross-linking process). In addition, since the second collagen of the second layer 132 undergoes a cross-linking reaction in an acidic condition (i.e. the second collagen is acidic when subjected to a cross-linking process), the obtained shield element exhibits a relatively high light transmittance.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

0.5 g of polyvinylpyrrolidone (PVP, with a weight average molecular weight of about 50,000-60,000) was added into a reaction bottle, and then 50 mL of pure water was added into the reaction bottle. After heating and stirring until the polyvinylpyrrolidone (PVP) was completely dissolved, a polyvinylpyrrolidone (PVP) aqueous solution was obtained. Next, the polyvinylpyrrolidone (PVP) aqueous solution was titrated with a hydrochloric acid aqueous solution (with a concentration of 6N) until the polyvinylpyrrolidone (PVP) aqueous solution has a pH value of less than about 3. Next, 0.5 g of collagen (fibrous, with a fiber length of about 15 mm) and pilocarpine were added into the reaction bottle, and the result was stirred until the collagen was completely dissolved. Herein, the result had a pilocarpine concentration of 0.05 wt % (based on the weight of the solution). Next, the obtained solution was poured into a mold (arbitrary two-dimensional module size), and then cooled down to 4° C.

Next, 50 mL of zinc acetate aqueous solution (0.5 M) was mixed with 50 mL polyvinylpyrrolidone (PVP) aqueous solution (1.25 wt %), and the mixture was heated to 80° C. and then stirred for 30 minutes. Next, a sodium hydroxide aqueous solution (1 M) was slowly added into the mixture until the obtained solution had a pH value of 11. After cooling, 100 ml of acetone was added into the solution to obtain a white zinc-oxide-containing solid, and the result was subjected to centrifugation and then the upper-layer liquid was removed. The result was stirred with water, ethanol and acetone in sequence, subjected to centrifugation, and then the upper-layer liquid was removed. Finally, the result was dried to obtain zinc oxide. 1 g of zinc oxide was added into a sodium hydroxide aqueous solution (0.2M) and then dispersed uniformly to obtain a zinc oxide aqueous solution with a pH value of 11. The zinc oxide aqueous solution was poured into a mold. After standing at 4° C. for 24 hours, the liquid in the mold was removed, and the remaining film in the mold was washed with water until the film was neutral.

Next, the film was removed from the mold, and then dried at room temperature. Next, the obtained film was disposed in a chamber for 1 hour to undergo a cross-linking reaction to obtain Sample (I), in which the chamber has saturated vapor of formaldehyde gas.

Comparative Example 1

0.8 g of polyvinylpyrrolidone (PVP, with a weight average molecular weight of about 50,000-60,000) was added into a reaction bottle, and 100 mL of pure water was added into the reaction bottle. After stirring until the polyvinylpyrrolidone (PVP) was completely dissolved, a polyvinylpyrrolidone (PVP) aqueous solution was obtained. Next, the polyvinylpyrrolidone (PVP) aqueous solution was titrated with a hydrochloric acid aqueous solution (with a concentration of 6N) until the polyvinylpyrrolidone (PVP) aqueous solution has a pH value of less than about 3. Next, 0.8 g of collagen (fibrous, with a fiber length of about 15 mm) was added into a reaction bottle, and the result was stirred until the collagen was completely dissolved. Next, the obtained solution was poured into a mold (arbitrary two-dimensional module size), and then dried at room temperature to obtain a film. Next, the film was disposed in a chamber under the saturated vapor of formaldehyde gas for 1 hour to undergo a cross-linking reaction, and the cross-linked film was soaked in a pilocarpine-containing aqueous solution (with a pilocarpine concentration of 2 wt %, based on the weight of the solution) for 30 hours- to obtain Sample (II).

Comparative Example 2

0.8 g of polyvinylpyrrolidone (PVP, with a weight average molecular weight of about 50,000-60,000) was added into a reaction bottle, and 100 mL of pure water was added into the reaction bottle. After stirring until the polyvinylpyrrolidone (PVP) was completely dissolved, a polyvinylpyrrolidone (PVP) aqueous solution was obtained. Next, the polyvinylpyrrolidone (PVP) aqueous solution was titrated with a hydrochloric acid aqueous solution (with a concentration of 6N) until the polyvinylpyrrolidone (PVP) aqueous solution has a pH value of less than about 3. Next, 0.8 g of collagen (fibrous, with a fiber length of about 15 mm), 0.35 g of zinc oxide and pilocarpine were added into a reaction bottle, and the result was stirred until the collagen was completely dissolved. Herein, the result had a pilocarpine concentration of 0.4 wt % (based on the weight of the solution). Next, the obtained solution was poured into a mold (arbitrary two-dimensional module size), and then dried at room temperature to obtain a film. Next, the film was disposed in a chamber under the saturated vapor of formaldehyde gas for 1 hour to undergo a cross-linking reaction to obtain Sample (III).

Drug Release Test

A drug release chamber (which was a cylinder having a diameter of 15 mm, a height of 1 mm and a volume of 177 μL). Samples (I)-(III) were cut into films with a thickness of 0.9 mm and a diameter of 14.5 mm individually. Next, the films of Samples (I)-(III) were subjected to a drug release test, and the results were shown in FIG. 6. The drug release test included following steps. The film of sample was disposed in the drug release chamber, and water (serving as an eluent) was introduced into the drug release chamber. Next, the eluent released from the drug release chamber was collected and then subjected to a drug concentration analysis by high performance liquid chromatography (HPLC).

Figure 6:
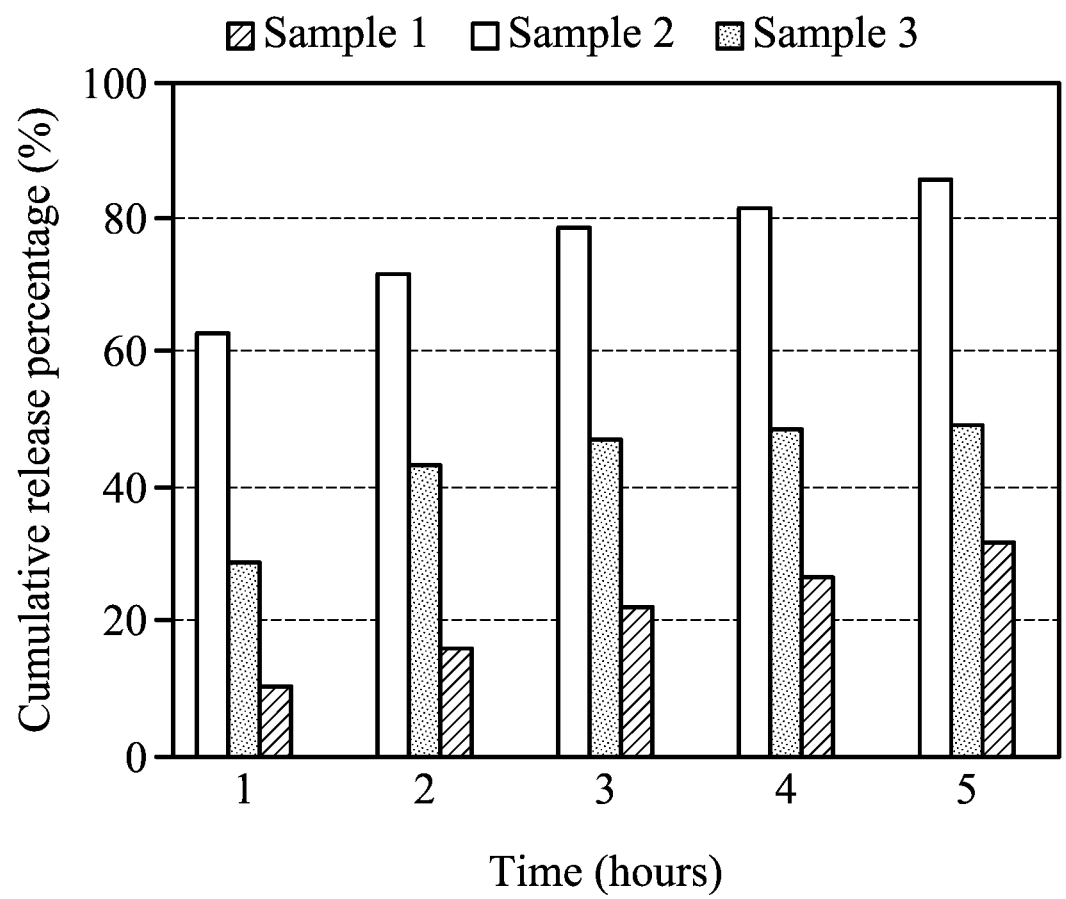
FIG. 6 is a graph showing the relationship between cumulative release amount of the drug release samples of Examples and Comparative Examples against time.

As shown in FIG. 6, Sample (II) (which was prepared by soaking in drug merely) exhibited a cumulative release percentage of 60% in the first hour, thereby exhibiting poor sustained release ability in comparison with other samples. Sample (III) was prepared from a composite material (constituted by collagen and hydrophilic biodegradable polymer) further including metal oxide. Since the collagen of Sample (III) was acidic during cross-linking, the Sample (III) had a less ideal sustained release ability. Sample (I) was the material of the drug release element of the ophthalmic drug delivery device of the disclosure. In comparison with Sample (II) and Sample (III), since the collagen of Sample (I) was neutral (i.e. cured in a neutral condition) during cross-linking, the drug would be tightly embedded by the composite material (constituted by collagen and hydrophilic biodegradable polymer), thereby achieving the effect of long-term drug delivery with constant rate release.

Example 2

0.5 g of polyvinylpyrrolidone (PVP, with a weight average molecular weight of about 50,000-60,000) was added into a reaction bottle, and 100 mL of pure water was added into the reaction bottle. After stirring until the polyvinylpyrrolidone (PVP) was completely dissolved, a polyvinylpyrrolidone (PVP) aqueous solution was obtained. Next, the polyvinylpyrrolidone (PVP) aqueous solution was titrated with a hydrochloric acid aqueous solution (with a concentration of 6N) until the polyvinylpyrrolidone (PVP) aqueous solution has a pH value of less than about 3. Next, 0.5 g of collagen (fibrous, with a fiber length of about 15 mm) was added into a reaction bottle, and the result was stirred until the collagen was completely dissolved. Next, the obtained solution was poured into a mold (arbitrary two-dimensional module size), and then dried at room temperature to obtain a film. Next, the film was disposed in a chamber under the saturated vapor of formaldehyde gas for 1 hour to undergo a cross-linking reaction to obtain Sample (IV).

Example 3

0.8 g of polyvinylpyrrolidone (PVP, with a weight average molecular weight of about 50,000-60,000) was added into a reaction bottle, and 100 mL of pure water was added into the reaction bottle. After stirring until the polyvinylpyrrolidone (PVP) was completely dissolved, a polyvinylpyrrolidone (PVP) aqueous solution was obtained. Next, the polyvinylpyrrolidone (PVP) aqueous solution was titrated with a hydrochloric acid aqueous solution (with a concentration of 6N) until the polyvinylpyrrolidone (PVP) aqueous solution has a pH value of less than about 3. Next, 0.8 g of collagen (fibrous, with a fiber length of about 15 mm) and pilocarpine were added into a reaction bottle, and the result was stirred until the collagen was completely dissolved. Herein, the result had a pilocarpine concentration of 0.4 wt % (based on the weight of the solution). Next, the obtained solution was poured into a mold (arbitrary two-dimensional module size), and then dried at room temperature to obtain a film. Next, the film was disposed in a chamber under the saturated vapor of formaldehyde gas for 1 hour to undergo a cross-linking reaction to obtain Sample (V).

Example 4

1 g of polyvinylpyrrolidone (PVP, with a weight average molecular weight of about 50,000-60,000) was added into a reaction bottle, and 100 mL of pure water was added into the reaction bottle. After stirring until the polyvinylpyrrolidone (PVP) was completely dissolved, a polyvinylpyrrolidone (PVP) aqueous solution was obtained. Next, the polyvinylpyrrolidone (PVP) aqueous solution was titrated with a hydrochloric acid aqueous solution (with a concentration of 6N) until the polyvinylpyrrolidone (PVP) aqueous solution has a pH value of less than about 3. Next, 1 g of collagen (fibrous, with a fiber length of about 15 mm) and timolol maleate were added into a reaction bottle, and the result was stirred until the collagen was completely dissolved. Herein, the result had a timolol maleate concentration of 0.3 wt % (based on the weight of the solution). Next, the obtained solution was poured into a mold (arbitrary two-dimensional module size), and then dried at room temperature to obtain a film. Next, the film was disposed in a chamber under the saturated vapor of formaldehyde gas for 1 hour to undergo a cross-linking reaction to obtain Sample (VI).

Example 5

0.35 g of polyvinylpyrrolidone (PVP, with a weight average molecular weight of about 50,000-60,000) was added into a reaction bottle, and then 12 mL of pure water was added into the reaction bottle. After stirring until the polyvinylpyrrolidone (PVP) was completely dissolved, a polyvinylpyrrolidone (PVP) aqueous solution was obtained. Next, the polyvinylpyrrolidone (PVP) aqueous solution was titrated with a hydrochloric acid aqueous solution (with a concentration of 6N) until the polyvinylpyrrolidone (PVP) aqueous solution has a pH value of less than about 3. Next, 0.35 g of collagen (fibrous, with a fiber length of about 15 mm) and latanoprost were added into a reaction bottle, and the result was stirred until the collagen was completely dissolved. Herein, the result had a latanoprost concentration of 0.005 wt % (based on the weight of the solution). Next, the obtained solution was poured into a mold (arbitrary two-dimensional module size), and then dried at room temperature to obtain a film. Next, the film was disposed in a chamber under the saturated vapor of formaldehyde gas for 1 hour to undergo a cross-linking reaction to obtain Sample (VII).

Light Transmittance Test

The light transmittance of Sample (I), Sample (IV), Sample (V), Sample (VI) and Sample (VII) were determined, and the results were as shown in Table 1. The light transmittance of the film was determined by measuring the light absorption coefficient in the wavelength range of 350 nm to 700 nm of the film (under the condition of wet film, that is, when the water content of the film is saturated) via a spectrophotometer. Then the light absorption coefficient was converted into light transmittance.

TABLE 1

|  | Sample (I) | Sample (IV) | Sample (V) | Sample (VI) | Sample (VII) |
| --- | --- | --- | --- | --- | --- |
| light transmittance | 60% | 90% | 18% | 70% | 7% |

Sample (IV) was the material of the shield element of the ophthalmic drug delivery device of the disclosure. Since the collagen of Sample (IV) was acidic during cross-linking, Sample (IV) could have a light transmittance of 90%, resulting that the vision of the user would not be interfered, and can protect the wound from contact during healing.

It will be clear that various modifications and variations can be made to the disclosed methods and materials. It is intended that the specification and examples be considered as exemplary only, with the true scope of the disclosure being indicated by the following claims and their equivalents.

What is claimed is:

1. An ophthalmic drug delivery device, comprising:
   a shield element, which is adapted to be positioned onto a visual region of a cornea, wherein the shield element has a light transmittance more than or equal to 80%; and
   a drug release element, which is adapted to be positioned onto a region surrounding the cornea, wherein the region is outside the cornea, wherein the drug release element is an annular body, and the drug release element surrounds the shield element,
   wherein the drug release element is neutral and comprises a cross-linked neutral collagen, a first hydrophilic biodegradable polymer and a drug, and wherein the shield element is acidic and comprises a cross-linked acidic collagen and a second hydrophilic biodegradable polymer.

2. The ophthalmic drug delivery device as claimed in claim 1, wherein the weight ratio of the cross-linked neutral collagen to the first hydrophilic biodegradable polymer is ranging from 1:3 to 9:1.

3. The ophthalmic drug delivery device as claimed in claim 1, wherein the weight ratio of the cross-linked neutral collagen to the second hydrophilic biodegradable polymer is ranging from 1:3 to 9:1.

4. The ophthalmic drug delivery device as claimed in claim 1, wherein the amount of the drug is ranging from 0.01 wt % to 20 wt %, based on the total weight of the neutral collagen and the first hydrophilic biodegradable polymer.

5. The ophthalmic drug delivery device as claimed in claim 1, wherein the ophthalmic drug release element is a product obtained by subjecting a first layer to a cross-linking process in the presence of a cross-linking agent, wherein the first layer is a product obtained by solidifying a neutral aqueous solution, and the neutral aqueous solution includes water, a first collagen, the first hydrophilic biodegradable polymer, and the drug.

6. The ophthalmic drug delivery device as claimed in claim 5, wherein the neutral aqueous solution has a pH value of 6.5 to 7.5.

7. The ophthalmic drug delivery device as claimed in claim 1, wherein the shield element is a product obtained by subjecting a second layer to a cross-linking process in the presence of a cross-linking agent, wherein the second layer is formed by drying an acidic aqueous solution, and the acidic aqueous solution includes water, a second collagen and the second hydrophilic biodegradable polymer.

8. The ophthalmic drug delivery device as claimed in claim 7, wherein the acidic aqueous solution has a pH value of 2 to 5.

9. The ophthalmic drug delivery device as claimed in claim 1, wherein the first hydrophilic biodegradable polymer and the second hydrophilic biodegradable polymer are independently selected from a group consisting of polyvinyl alcohol (PVA), polyethylene glycol/polyethylene oxide (PEG/PEO) and polyvinylpyrrolidone (PVP).

10. The ophthalmic drug delivery device as claimed in claim 1, wherein the ophthalmic drug release element comprises a metal oxide doped in the drug release element, wherein the metal oxide is zinc oxide, iron oxide, or a combination thereof.

11. The ophthalmic drug delivery device as claimed in claim 5, wherein the cross-linking agent is formaldehyde, glutaraldehyde, glyoxal, malonaldehyde, succinaldehyde, phthalaldehyde, dialdehyde starch, polyacrolein, polymethacrolein, or a combination thereof.

12. The ophthalmic drug delivery device as claimed in claim 1, wherein the drug is apraclonidine, timolol maleate, betaxolol, levobunolol, atenolol, metipranolol, timolol hemihydrate, pilocarpine, carbachol, travoprost, bimatoprost, tafluprost, latanoprost, netarsudil, polyvinyl alcohol hypromellose, glycerine, pegaptanib, propylene glycol, tetryzoline, cyclosporine, doxycicine, vitamin D3, quinethazone, hydroxypropyl cellulose, polyvinylpyrrolidone, chlorobutanol, bepotastine besilate, lifitegrast, omega-3 fatty acids, flaxseed oil, carboxymethyl cellulose, hyaluronic acid, hydroxypropyl-guar, macrolide, tetracycline, tacrolimus, acetylcysteine, vitamin A, carbomer, triglycerides, fluorometholone, loteprednol, fluocinolone, dexamethasone, difluprednate, triamcinolone, prednisolone, rimexolone, gentamicin, tobramycin, besifloxacin, ciprofloxacin, gatifloxacin, levofloxacin, moxifloxacin, ofloxacin, azithromycin, erythromycin, bacitracin, natamycin, neomycin, polymyxin B, trimethoprim, sulfacetamide, bromfenac, ketorolac, nepafenac, flurbiprofen, or diclofenac.

13. A method for fabricating an ophthalmic drug delivery device, which is the ophthalmic drug delivery device as claimed in claim 1, comprising:
providing a first aqueous solution, wherein the first aqueous solution comprises water, a first collagen, a first hydrophilic biodegradable polymer, a first acidic substance, and a drug, and the first aqueous solution has a pH value of 2 to 5;
pouring the first aqueous solution into a first mold, and then the first mold is cooled down to a temperature of 1° C. to 10° C.;
pouring a second aqueous solution into the first mold, wherein the second aqueous solution comprises an alkali metal hydroxide and water, and the second aqueous solution has a pH value of 9 to 11;
standing the first mold to transfer the first aqueous solution into a first layer, wherein the first layer has a central region and an annular region, and the annular region surrounds the central region and is coaxial with the central region;
removing the central region from the first layer so that the remaining first layer has a through hole after removing the second aqueous solution from the first mold;
filling the through hole with the third aqueous solution, wherein the third aqueous solution comprises water, a second collagen, a second acidic substance, and a second hydrophilic biodegradable polymer, wherein the third aqueous solution has a pH value of 2 to 5;
subjecting the third aqueous solution to a drying process to obtain a second layer, wherein the first layer and the second layer constitute a composite film;
disposing the composite film in a second mold to obtain a molded film after molding; and
subjecting the composite film to a cross-linking process by a cross-linking agent to obtain the ophthalmic drug delivery device.

14. The method as claimed in claim 13, wherein a step for preparing the first aqueous solution comprises:
dissolving the first collagen, the first hydrophilic biodegradable polymer and the drug in water to obtain a first mixture, wherein the weight ratio of the first collagen to the first hydrophilic biodegradable polymer is ranging from 1:3 to 9:1, and the amount of the drug is ranging from 0.01 wt % to 20 wt %, based on the total weight of the first collagen and the first hydrophilic biodegradable polymer; and
adding the first acidic substance to the first mixture until the obtained first aqueous solution has a pH value of 2 to 5, wherein the first aqueous solution has a solid content ranging from 0.5 wt % to 10 wt %.

15. The method as claimed in claim 13, wherein the second aqueous solution further comprises a metal oxide.

16. The method as claimed in claim 15, wherein a step for preparing the second aqueous solution comprises:
providing an alkali metal hydroxide aqueous solution, wherein the alkali metal hydroxide aqueous solution has a concentration ranging from 0.1 M to 2 M;
dissolving the metal oxide in the alkali metal hydroxide aqueous solution to obtain the second aqueous solution, wherein the amount of the metal oxide is ranging from 0.5 wt % to 2 wt %, based on the weight of the second aqueous solution, wherein the second aqueous solution has a pH value of 9 to 11.

17. The method as claimed in claim 13, after removing the second aqueous solution from the first mold, further comprising washing the first layer with water until the first layer is neutral.

18. The method as claimed in claim 13, wherein a step for preparing the third aqueous solution comprises:
dissolving the second collagen and the second hydrophilic biodegradable polymer in water to obtain a third mixture, wherein the weight ratio of the second collagen to the second hydrophilic biodegradable polymer is ranging 1:3 to 9:1; and
adding the second acidic substance to the third mixture until the third aqueous solution has a pH value of 2 to 5, wherein the third aqueous solution has a solid content ranging from 0.5 wt % to 10 wt %.

19. The method as claimed in claim 13, wherein the first hydrophilic biodegradable polymer and the second hydrophilic biodegradable polymer are independently selected from a group consisting of polyvinyl alcohol (PVA), polyethylene glycol/polyethylene oxide (PEG/PEO) and polyvinylpyrrolidone (PVP).

20. The method as claimed in claim 13, after subjecting the composite film to a cross-linking process, further comprising cutting the composite film to form the ophthalmic drug delivery device with a diameter ranging from 12 mm to 16 mm.

* * * * *